United States Patent [19]

Winston

[11] Patent Number: 4,895,875

[45] Date of Patent: Jan. 23, 1990

[54] STABILIZED PEROXIDE SOLUTIONS

[75] Inventor: Anthony E. Winston, East Brunswick, N.J.

[73] Assignee: Church & Dwight Co., Inc., Princeton, N.J.

[21] Appl. No.: 206,180

[22] Filed: Jun. 13, 1988

[51] Int. Cl.$^4$ ............................................. A61K 31/17
[52] U.S. Cl. .................................... 514/588; 514/972; 424/616; 564/2
[58] Field of Search ................... 514/588, 714; 564/2, 564/972; 560/182

[56] References Cited

U.S. PATENT DOCUMENTS

| | | | |
|---|---|---|---|
| 1,040,665 | 10/1912 | Gruter et al. | 564/3 |
| 1,051,926 | 2/1913 | Stockelbach | 564/3 |
| 1,071,186 | 8/1913 | Stern | 514/588 |
| 1,153,985 | 9/1915 | Weber | 564/3 |
| 1,210,570 | 1/1917 | Weber | 564/3 |
| 2,259,479 | 10/1941 | Morgan | 564/3 |
| 2,430,450 | 11/1947 | Brown | 514/588 |

Primary Examiner—Douglas W. Robinson
Assistant Examiner—Zohreh A. Fay
Attorney, Agent, or Firm—Bryan, Cave, McPheeters & McRoberts

[57] ABSTRACT

Solutions of urea peroxide in glycerine suitable for use as ear wax removal aid formulations, which solutions have been stabilized by the addition of succinic anhydride thereto.

9 Claims, No Drawings

STABILIZED PEROXIDE SOLUTIONS

FIELD OF THE INVENTION

This invention relates to a method for stabilizing pharmaceutical solutions for generating hydrogen peroxide, and to the stabilized solutions thus prepared. More particularly, it relates to the stabilization of urea peroxide solutions in glycerine as ear wax removal aid formulations or for similar purposes.

BACKGROUND OF THE INVENTION

Hydrogen peroxide-generating pharmaceutical preparations for the removal of ear wax and the like have been known for many years. According to the U.S. Food & Drug Administration monograph on optic products, ear wax removal formulations must contain 6.5% urea peroxide formulated in an anhydrous glycerine base.

In order to provide maximum peroxide stability, it is generally accepted that it is important to minimize any traces of moisture (water) in the product. However, even with extremely dry glycerine, there is a tendency for decomposition of the product. As the hydrogen peroxide decomposes, it releases oxygen, leaving moisture in the product which further catalyzes decomposition of the peroxide. Thus, there is a need for a stabilizing agent even in the initial absence of moisture.

Manufacturers of currently marketed ear wax removal aid formulations utilize a number of different techniques for stabilizing their products. In addition to urea peroxide and glycerine, one formulation (Murine Ear Drops) lists alcohol, Polysorbate 20 and other ingredients as contents of the product. A second product (Debrox Drops) also contains citric acid, propylene glycol, sodium stannate, water and other ingredients. These additional ingredients are presumably present to enhance product stability.

Many ways of stabilizing urea peroxide have been described in the patent literature. See, for example, U.S. Pat. Nos. 2,259,479; 1,051,926; 1,153,985; 1,210,570; 1,071,186; and 1,040,665. However, the products described in these patents are either insufficiently soluble in anhydrous glycerine base (e.g., sodium phosphate, sodium bitartrate, boric acid, pyrophosphates, metaphosphates, sodium bisulfate, sodium stannate, etc.), of questionable safety for pharmaceutical use (e.g., phenacetin, tannic acid, benzoylecgonine, protalbic acid, acetanilide, 8-hydroxyquinoline, etc.) or insufficiently effective (e.g., 8-hydroxyquinoline, acetanilide, sodium stannate, etc.) Additionally, some materials such as 8-hydroxyquinoline impart an unacceptable orange color to the product.

It is among the objects of the present invention to provide a new technique for stabilizing glycerine-urea peroxide pharmaceutical solutions, which requires only the use of a single stabilizing ingredient and which may be readily commercially employed to provide solutions useful as ear wax removal formulations having superior stability characteristics.

SUMMARY OF THE INVENTION

In accordance with the invention, a method for stabilizing a hydrogen peroxide generating pharmaceutical solution consisting essentially of from about 1 to 12% urea peroxide in glycerine, and containing no more than about 1% water, is provided, which method comprises:

(a) dissolving succinic anhydride in at least a portion of the glycerine, in an amount equivalent to from about 0.01 to 30% of the final solution;

(b) when it is desired to pre-blend the succinic anhydride with only a portion of the glycerine in step (a), thereafter admixing any remaining portion of the glycerine to make up the final solution;

(c) mixing the solution for a period sufficient to permit the anhydride to react with the glycerine;

(d) adding the urea peroxide to the thus treated solution; and (e) blending the resulting mixture to form the desired stabilized solution Urea peroxide, which is also known as urea hydrogen peroxide, carbamide peroxide, or hydrogen peroxide carbamide, has the formula $CO(NH_2)_2 \cdot H_2O_2$. It readily releases hydrogen peroxide when dissolved in glycerine in proportions of from as little as about 1% to as much as about 20% thereof. It has been found in accordance with the present invention that the addition of succinic anhydride imparts increased peroxide stability to such solutions, particularly to those incorporating from about 5.5 to 7.5% urea peroxide. The addition of as little as about 0.02% succinic anhydride to urea peroxideglycerine solutions containing from about 1 to 12% urea peroxide has been shown to impart some increased peroxide stability thereto. Preferably, however, succinic anhydride is added to such formulations in amounts of from about 0.5% to 1.5%, based on the weight of the stabilized solution.

A stabilized peroxide-generating solution is thus prepared, which consists essentially of from about 1 to 12% urea peroxide in the glycerine solvent and contains, as a stabilizing agent therefor, the reaction product of the succinic anhydride and the glycerine. The stabilized solution may be readily employed, without the addition of further ingredients, as an ear wax removal formulation or for similar applications, e.g., as a 10% solution of urea peroxide in glycerine for oral inflammation and canker sores.

It has been found that the addition of succinic anhydride to glycerine prior to admixing urea peroxide therewith greatly increases the storage stability of the peroxide to the loss of active oxygen. It is believed that the succinic anhydride reacts with the glycerine, forming the glyceryl succinate half ester:

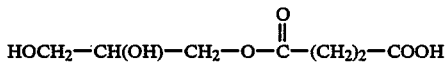

which material is the active peroxide stabilizer.

The mechanism of the increased stability thus afforded is not known. The glyceryl succinate may, however, interfere with catalytic breakdown of the peroxide due to the presence of trace impurities in the solution. In addition, when trace levels of moisture are present in the nominally anhydrous glycerine, the succinic anhydride preferentially reacts therewith, forming succinic acid, drying the glycerine, and further preventing decomposition of the urea peroxide.

It will be understood that the foregoing proposed mechanism is illustrative only, and that the present invention is not limited to the formation of glyceryl succinate as the active stabilizing agent, or to the interference by that material with the catalytic breakdown of urea peroxide.

The stabilizing technique of the invention is carried out by initially dissolving the succinic anhydride additive, preferably in an amount of from about 0.5 to 1.5% of the stabilized solution, in the glycerine solvent, preferably with heating to temperatures of at least 50° C., most desirably to about 60°–90° C. The succinic anhydride may be directly dissolved in all of the glycerine solvent, which typically comprises from about 85% to 98% of the stabilized solution. Alternatively, the succinic anhydride may be pre-blended in a portion, e.g., from about 5 to 50%, most desirably about 20%, of the glycerine, after which the remaining portion of the glycerine may be admixed therewith to make up the total solution.

Whether pre-blended with a portion of the glycerine or admixed directly with all of the glycerine, the solution containing the succinic anhydride is mixed for sufficient time (usually for about 30 minutes) to allow the dissolved anhydride to completely react with the glycerine. After cooling below about 55° C., desirably to about 35° C. to 40° C., the urea peroxide is added to the treated solution and the mixture is blended until dissolution is complete and the desired stabilized solution is formed.

The improved peroxide stability characteristics achieved in accordance with the invention are illustrated in the following examples. Unless otherwise indicated, all parts and percentages in the following examples or otherwise specified hereinabove, are given in parts by weight, and all temperatures are in degrees Celsius.

DETAILED DESCRIPTION OF PREFERRED EMBODIMENTS

EXAMPLES 1–3

Comparison of Peroxide Stability with the Addition of Varying Amounts of Succinic Anhydride to a Urea Peroxide-Glycerine Solution Glycerine was heated to about 50° C., varying amounts of succinic anhydride were then added to the glycerine, and the mixture was stirred for about 30–60 minutes while maintaining the temperatures below 60° C., to effect complete solution. After cooling to about 40° C., urea peroxide was added and blended to form stabilized solutions containing 6.5% urea peroxide.

The resulting solutions, together with a control formulation consisting of 6.5% urea peroxide in glycerine (Control A) were stored at room temperature or at 44° C. for up to 12 weeks. Samples of the respective test solutions were analyzed after varying periods for active hydrogen peroxide by accurately weighing about 1 g of product and transferring it to a 250 ml iodine flask with the aid of water. Glacial acetic acid (5 ml) was added and the solution mixed. Potassium iodide (2 g) and 1 drop of ammonium molybdate solution were added and the mixture was stored for 10 minutes. The liberated iodine was titrated with 0.1N sodium thiosulfate, adding starch solution as an indicator as the end point was approached. The peroxide content was determined as follows:

$$\% \text{ H}_2\text{O}_2 = \frac{\text{mls (thiosulfate)} \times 0.1\text{N} \times 34 \times 100}{1000 \times 2 \times \text{Wt (product)}}$$

$$\% \text{ H}_2\text{O}_2 \text{ Remaining} = \frac{\% \text{ H}_2\text{O}_2 \text{ present} \times 100\%}{\% \text{ H}_2\text{O}_2 \text{ initial}}$$

The percentages of hydrogen peroxide remaining, as percentages of the initial hydrogen peroxide present in the various test and control solutions, are specified below.

TABLE I

| Example or Control | Succinic Anhydride Added (% of Stabilized Solution) | % H$_2$O$_2$ Remaining After Storage for Weeks Shown | | | | | |
|---|---|---|---|---|---|---|---|
| | | At 44° C. | | | At Room Temperature | | |
| | | 1 Wk | 4 Wks | 6 Wks | 1 Wk | 5 Wks | 12 Wks |
| Ex. 1 | 0.5 | 95 | 89 | 81 | — | 96 | 97 |
| Ex. 2 | 0.2 | 100 | 85 | 63 | — | 97 | 87 |
| Ex. 3 | 0.05 | 100 | — | 64 | — | 98 | — |
| Control A | 0 | 23 | — | — | 60 | — | — |

The results given in Table I indicate that the peroxide stability of the urea peroxide-glycerine solution is increased by the addition of succinic anhydride, and that greater long-term stability is obtained utilizing higher levels of the anhydride.

Example 4

Comparison of Urea Peroxide-Glycerine Solution Stabilized with 1% Added Succinic Anhydride and Prior Formulations A formulation containing 1% added succinic anhydride (by weight of the final preparation) and 7.2% urea peroxide was prepared in the same manner as described in connection with Examples 1–3 above. Samples of the thus stabilized solution, a control preparation containing 7.2% urea peroxide without stabilizer (Control A), and samples of the commercial "Debrox" and "Murine" ear wax removal aid formulations (Controls B and C, respectively) were stored for varying periods at 44° C. The percentages of hydrogen peroxide remaining (based on the initial H$_2$O$_2$ content in the respective samples), determined as described above, were as follows:

TABLE II

| Weeks Storage at 44° C. | Example 4 with 1% added Succinic Anhydride | Control A with no Stabilizer | Control B "Debrox" | Control A "Murine" |
|---|---|---|---|---|
| 46 days | 81% | 0% | 72% | 68% |
| 56 days | 71% | 0% | 66% | 56% |
| 70 days | 67% | 0% | 51% | 46% |
| 84 days | 60% | 0% | 47% | 32% |

Examples 5–8

Stabilization of Urea Peroxide-Glycerine Solutions Having various Moisture Contents The following experiments were carried out to demonstrate the low degree of sensitivity of the succinic anhydride-stabilized urea peroxide-glycerine solution to low levels of moisture in the glycerine solvent used to make up the product. Succinic anhydride was added (in amounts equivalent to 0.5% and 0.2% of the final solution) to glycerine to which amounts varying from 0 to 0.5% by weight of water had been previously added. Urea peroxide (in an amount of 6.5% of the stabilized solution) was then added, in the same manner as described above in connection with Examples 1–3.

After storage at both ambient and elevated temperatures for varying periods, the amount of residual peroxide as a percentage of the initial hydrogen peroxide content was determined in the same manner as above. The following results were obtained:

TABLE III

| Example | Succinic Anhydride Level | H2O Added | At 44° C. 1 Wk | 4 Wks | 6 Wks | % of the Initial H2O Left After Given Weeks Storage At Room Temperature 4 Wks | 8 Wks |
|---|---|---|---|---|---|---|---|
| 5 | 0.5 | 0 | 93 | 87 | 79 | 94 | 95 |
| 6 | 0.5 | 0.5 | 100 | 94 | 82 | 100 | 94 |
| 7 | 0.2 | 0 | 100 | 85 | 63 | 97 | 98 |
| 8 | 0.2 | 0.4 | 100 | 59 | — | 100 | 99 |

From the preceding, it may be seen that better peroxide stabilities were demonstrated by the stabilized solutions of the invention as compared, for example, with Control A, notwithstanding the presence of the equivalent of up to a 0.5% moisture level in the glycerine, especially with product to which the higher level of succinic anhydride had been added.

Example 9

Comparison of the Addition of Different Stabilizers to Urea Peroxide-Glycerine Solutions The stabilities of further test formulations prepared in the same manner as described above, containing 6.5% urea peroxide, and 0.5% added succinic anhydride (Example 9), 0.5% acetanilide (Control D) and 0.5% 8-hydroxyquinoline (Control E) were compared by storage for varying periods at 40° C. and measurement of the residual hydrogen peroxide contents as aforesaid. The following results were obtained:

TABLE IV

| Period of Storage | % H2O2 Left After Given Weeks Storage at 40° C. | | |
|---|---|---|---|
| | Example 9 with 0.5% Succinic Anhydride | Control D 0.5% Acetanilide | Control E 0.5% 8-hydroxy-quinoline |
| 4 weeks | 89% | 85% | 83% |
| 8 weeks | 79% | 66% | 62% |

The results show the superior stability of the product to which succinic anhydride had been added, as compared with the control formulations. It may further be noted that acetanilide is known to oxidize to toxic aniline, nitrobenzene and acetic cid in the presence of hydrogen peroxide, and therefore would not be suitable for pharmaceutical use. 8-hydroxyquinoline, on the other hand, turns the product an extremely undesirable orange color.

Citric acid, succinic acid and sodium stannate were also tested as possible stabilizing agents; each of these materials was insufficiently soluble in the glycerine to provide a stabilizing effect.

It will be understood that various changes may be made in the stabilizing techniques and the stabilized formulations illustrated above without departing from the scope of the present invention. Accordingly, the preceding description is intended as illustrative only, the scope of the invention to be construed in light of the following claims.

I claim:

1. A method for stabilizing a pharmaceutical solution for generating hydrogen peroxide, said solution consisting essentially of from 1 to 12% urea peroxide in glycerine, and containing no more than 1% water, which comprises:

(a) dissolving succinic anhydride in at least a portion of the glycerine solvent, in an amount equivalent to from 0.01 to 3% of the total solution;
   (b) admixing any remaining portion of the glycerine to make-up said solution;
   (c) mixing the solution;
   (d) adding urea peroxide to the thus treated solution; and
   (e) blending the resulting mixture to form the desired stabilized solution.

2. The method of claim 1, wherein the succinic anhydride is pre-dissolved in step (a) in all of the glycerine solvent incorporated in said solution.

3. The method of claim 1, wherein the succinic anhydride is pre-dissolved in step (a) in from 5% to 50% of the glycerine solvent incorporated in said solution, and the remaining portion of the glycerine is added to the resulting mixture in step (b).

4. The method of claim 1, wherein the solution formed in step (a) is heated to from 60° to 90° C. to dissolve the succinic anhydride and, prior to adding urea peroxide to the treated solution in step (d), said solution is cooled to below 55° C.

5. A stabilized pharmaceutical solution for generating hydrogen peroxide, consisting essentially of from 1 to 12% urea peroxide in glycerine and, as a stabilizing agent therefor, a solution of succinic anhydride in glycerine prepared in the manner set forth in steps (a)–(c) of claim 1, said stabilized solution containing no more than 1% water.

6. A stabilized pharmaceutical solution for generating hydrogen peroxide, which comprises the solution prepared by the method of claim 1.

7. A stabilized pharmaceutical solution for generating hydrogen peroxide, which comprises the solution prepared by the method of claim 2.

8. A stabilized pharmaceutical solution for generating hydrogen peroxide, which comprises the solution prepared by the method of claim 3.

9. A stabilized pharmaceutical solution for generating hydrogen peroxide, which comprises the solution prepared by the method of claim 4.

* * * * *